(12) United States Patent  
Miller

(10) Patent No.: US 8,320,985 B2  
(45) Date of Patent: Nov. 27, 2012

(54) TOUCH SCREEN INTERFACES WITH PULSE OXIMETRY

(75) Inventor: Seth Adrian Miller, Englewood, CO (US)

(73) Assignee: Empire Technology Development LLC, Wilmington, DE (US)

( * ) Notice: Subject to any disclaimer, the term of this patent is extended or adjusted under 35 U.S.C. 154(b) by 909 days.

(21) Appl. No.: 12/417,478

(22) Filed: Apr. 2, 2009

(65) Prior Publication Data

US 2010/0256470 A1  Oct. 7, 2010

(51) Int. Cl.  
*A61B 5/1455* (2006.01)  
*G06F 3/042* (2006.01)

(52) U.S. Cl. ...................................... 600/324

(58) Field of Classification Search ............ 600/324, 600/323  
See application file for complete search history.

(56) References Cited

U.S. PATENT DOCUMENTS

| | | | |
|---|---|---|---|
| 4,759,369 A * | 7/1988 | Taylor | 600/323 |
| 5,069,214 A * | 12/1991 | Samaras et al. | 600/323 |
| 6,327,376 B1 * | 12/2001 | Harkin | 382/124 |
| 6,337,918 B1 | 1/2002 | Holehan | |
| 6,526,315 B1 | 2/2003 | Inagawa et al. | |
| 6,560,352 B2 | 5/2003 | Rowe | |
| 6,707,257 B2 | 3/2004 | Norris | |
| 2005/0209515 A1 | 9/2005 | Hockersmith et al. | |
| 2006/0020216 A1 | 1/2006 | Oishi et al. | |
| 2007/0088207 A1 * | 4/2007 | Mannheimer et al. | 600/323 |
| 2007/0106172 A1 | 5/2007 | Abreu | |
| 2007/0123762 A1 * | 5/2007 | Crawford et al. | 600/328 |
| 2007/0183633 A1 | 8/2007 | Hoffman | |
| 2007/0225581 A1 * | 9/2007 | Diab et al. | 600/323 |
| 2007/0265513 A1 * | 11/2007 | Schenkman et al. | 600/363 |
| 2008/0009689 A1 * | 1/2008 | Benaron et al. | 600/323 |
| 2008/0082004 A1 | 4/2008 | Banet et al. | |
| 2008/0267456 A1 | 10/2008 | Anderson | |
| 2008/0285813 A1 | 11/2008 | Holm | |
| 2008/0317302 A1 | 12/2008 | Abdallah et al. | |
| 2009/0054751 A1 | 2/2009 | Babashan et al. | |

OTHER PUBLICATIONS

International Preliminary Report on Patentability in International Application No. PCT/US2010/029703 mailed on Oct. 13, 2011.  
Laurie Barclay MD; "*Pulse Carbon Monoxide Oximeter Screening May be Safe, Feasible*"; Medscape Medical News, Feb. 22, 2008; http://www.medscape.com/viewarticle.570531.  
Masimo "*Masimo Rainbow SET Pulse CO-Oximetry*" http://www.masimo.com/Rainbow/about.htm.  
Creaghbrown "*How does Pulse oximetry work?*" http://www.creaghbrown.co.uk/anae/pulsox.htm.  
International Search Report mailed Nov. 12, 2010 for Application No. PCT/US2010/029703.

\* cited by examiner

*Primary Examiner* — Max Hindenburg  
*Assistant Examiner* — Michael C Stout  
(74) *Attorney, Agent, or Firm* — Dorsey & Whitney LLP

(57) ABSTRACT

Examples of touch screen interfaces with pulse oximetry are generally described, along with examples of methods of determining pulse rate, blood oxygen level, or both, with a touch screen interface.

28 Claims, 6 Drawing Sheets

TOUCH SCREEN INTERFACES WITH PULSE OXIMETRY

BACKGROUND

Touch screens user interfaces generally employ a transparent touch screen substrate disposed over a display. In operation, a user touches the transparent touch screen substrate and the touch and often the location of the touch are detected. The touch may be detected in a variety of ways—for example, by sensing a change in capacitance at the location of the touch. In one example, frustrated total internal reflection (FTIR) techniques may be used to detect the location of the touch. A touch screen employing frustrated total internal reflection generally includes an optical energy source positioned to illuminate the transparent touch screen substrate such that there is total internal reflection within the transparent touch screen substrate. That is, the light waves are reflected completely internally between the surfaces of the transparent touch screen substrate. When a user contacts the transparent touch screen substrate, however, the contact affects the index of refraction of the material, and light is scattered out of the transparent touch screen substrate in the location of the contact. Sensors are positioned to detect this scattered light, and the location of the touch can then be determined. In a similar manner, diffusive laser imaging employs laser light shined across a screen. Contact with the screen perturbs the laser light, and the location of the touch may be determined. A user device employing touch screen technology may accordingly interact with a user based on the location of a touch.

Pulse oximetry utilizes optical energy to illuminate a fingertip and determine pulse rate and blood oxygenation. Two wavelengths may be used to illuminate the fingertip, one corresponding to an absorbance maxima of oxygenated hemoglobin (typically 660 nm), and another corresponding to the absorbance maxima of deoxygenated hemoglobin. (typically 910 nm). Generally, a pulse oximeter monitors the ratio of absorbance or reflection of one wavelength relative to another and determines the blood oxygenation level of the fingertip based on the ratio. The fraction of reflected or absorbed light may also fluctuate with pulse, the pulse oximeter may simultaneously measure pulse rate.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings.

DETAILED DESCRIPTION

Figure 1:
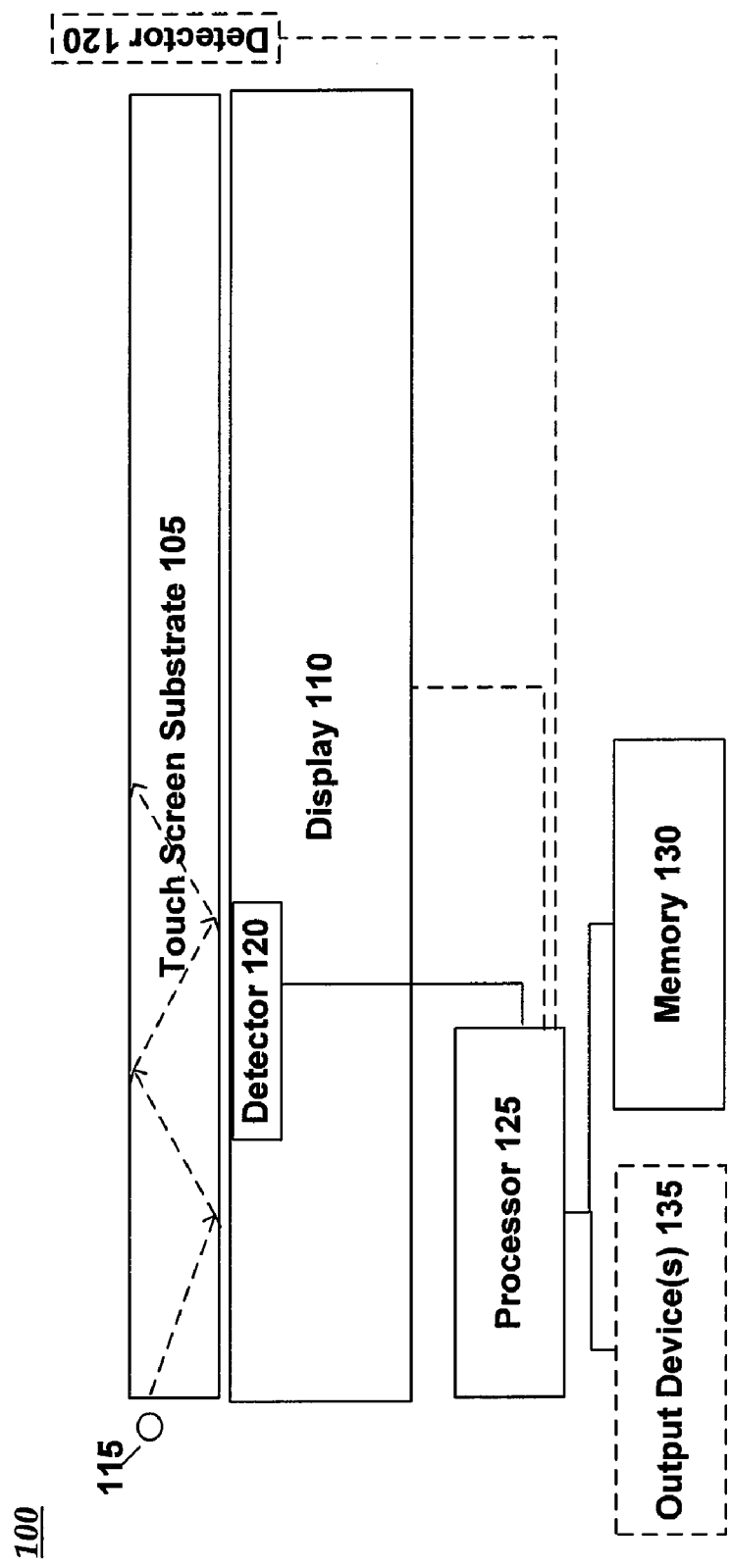
FIG. 1 is a schematic illustration of an example of a touch screen interface.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure. Certain details are set forth below to provide a sufficient understanding of described examples. However, it will be clear to one skilled in the art that the examples may be practiced without various of the particular details discussed. In some instances, for example, well-known circuits, control signals, and software operations have not been shown in detail in order to avoid unnecessarily obscuring the described examples.

FIG. 1 is a schematic illustration of an example of a touch screen interface 100 arranged in accordance with at least some embodiments of the present disclosure. An example of a cross-sectional portion of the touch screen interface 100 is also illustrated. FIG. 1 is intended to be explanatory and is not drawn to scale. The touch screen interface 100 may include a touch screen substrate 105, a display 110, an optical energy source 115, one or more detectors 120, a processor 125, a memory 130 and optional output devices 135.

The touch screen substrate 105 may be at least partially transparent such that light generated by a display 110 may be transmitted through the touch screen substrate 105. An example of a material that may be used to implement the touch screen substrate 105 is an acrylic pane.

An optical energy source 115 (or light source) may be positioned to illuminate the touch screen substrate 105. Examples of suitable optical energy sources may include light emitting diodes (LEDs) and lasers. Although a single optical energy source 115 is shown in FIG. 1, any number of optical energy sources may be provided and may be positioned along a length or width of the touch screen substrate 105.

The optical energy source 115 may emit light having a wavelength that is absorbed differently by oxygenated and deoxygenated hemoglobin. Typically, pulse oximeters make use of 660 nm and 910 nm light. The oxygenated blood may reflect more of the 660 nm light than deoxygenated blood, while deoxygenated blood may reflect more of the 910 nm light than oxygenated blood. Accordingly, in the example of a pulse detecting touch screen 100 of FIG. 1, the optical energy source 115 may emit light having a wavelength of either 660 nm or 910 nm. Other wavelengths may also be used that are appropriate for pulse rate detection in other examples.

Light emitted from the optical energy source 115 may be internally reflected within the touch screen substrate 105. When a user contacts the touch screen substrate 105, light emitted from the optical energy source 115 may experience frustrated internal reflection and pass through the touch screen substrate 105. A detector 120 may sense the light transmitted through the touch screen substrate 115 caused in part by the contact.

Although a single detector 120 is shown in FIG. 1, an array of detectors may be present adjacent to the touch screen substrate 105 to detect light transmitted through the touch screen substrate responsive to user contact. An array of detectors may be configured to detect a location of the contact. In other examples, detectors may be provided around a perimeter of the touch screen substrate 105. Generally, the detector 120 may be positioned anywhere that it may receive energy reflected from the touch screen substrate 105. In some examples, an array of such detectors may also be configured to provide location information about the contact. In some examples, the detector 120 may not be configured to provide information about the location of the contact, and location information may be obtained by other techniques using resistive or capacitive sensors (not shown in FIG. 1).

While the detector 120 is shown in the example of FIG. 1 positioned beneath the touch screen substrate 105, in other examples, the detector 120 may be positioned in different locations. For example, although the touch screen substrate 105 is shown in a horizontal orientation in FIG. 1, in other examples the touch screen substrate 105 may be in a vertical orientation, and the detector 120 may be positioned on either side of the touch screen substrate. In other embodiments, the detector 120 may be positioned to receive energy transmitted through a length of the touch screen substrate 105, as indicated by the alternative positioning of the detector 120 in FIG. 1 shown with dotted lines.

An example of a detector that may be used to implement the detector 120 may be a charge-coupled device (CCD). In some examples, one or more CCDs may be integrated into the display 110, however, in other examples the detector 120 may be separate from the display 110. Although not shown in FIG. 1, filters may be included at any point between the touch screen substrate 105 and the detector 120, where each filter may be configured to block out energy of different wavelengths than the wavelength emitted by the optical energy source 115.

The detector 120 may also be configured to detect a change in amplitude of the signal at the wavelength of light emitted by the energy source 115. The detected change in amplitude may correspond to a pulse rate associated with the user who contacted the touch screen substrate 105. Accordingly, the detector 120 may generate a detection signal corresponding to a pulse rate of a user, or a change in a pulse rate of a user.

A processor 125 may be coupled to the detector 120. The processor 125 may be configured to receive the detection signal from the detector corresponding to an amount of energy received at the wavelength emitted by the optical energy source 115. By analyzing variations in the strength of the received signal over time, the processor 125 may determine a pulse rate value related to the pulse rate of the user who contacted the touch screen substrate 105. The processor 125 may also be coupled to the display 110 in some examples. The processor 125 may be configured to couple control signals to the display 110 for the display of images or selections to a viewer of the display 110. In other examples, however, a different processor may be used to control the display of images than the processor that is used to detect a pulse rate. The processor 125 may also be coupled to the detector 120 and arranged to receive location information about a contact from the user. In other examples, the processor 125 may be coupled to other sensors (not shown) and arranged to obtain location information.

A memory 130 may be coupled to the processor 125. The memory 130 may be storing computer readable instructions, that, when executed, may cause the processor 125 to receive a signal from the detector 120 and determine a pulse rate value based on the changes in the received signal over time. The memory 130 may be encoded with instructions for computing the pulse rate value based on a detection signal or the memory may store a look-up table (LUT) for correlating measured signal changes associated with a pulse rate, for example. The memory 130 may also be arranged to store values associated with the pulse rate (i.e., a pulse rate value) of the user. More than one pulse rate value may be stored in memory 130 when a user contacts a touch screen multiple times over the course of a given use. Detected changes in pulse rate values may be used by the processor 125 to present a graphical representation of one or more pulse rate values on the display 110 or other components of a device in which the touch screen interface 100 may be used. For example, a numerical display or one or more graphical plots may be generated and displayed on the display 110 containing information about one or more pulse rate values.

The touch screen interface 100 shown in FIG. 1 may be used to determine a pulse rate associated with a user contacting the touch screen substrate 105. Once a pulse rate value has been determined, the value may be output to one or more output devices 135, which may include another display or a network connection for communication to remote devices. In some examples, the determined pulse rate value may be displayed on the display 110. Based on the determined pulse rate value, the image displayed on the display 110 may be altered. Examples of applications, methods or processes for using the touch screen interface 100 will be discussed further below.

Figure 2:
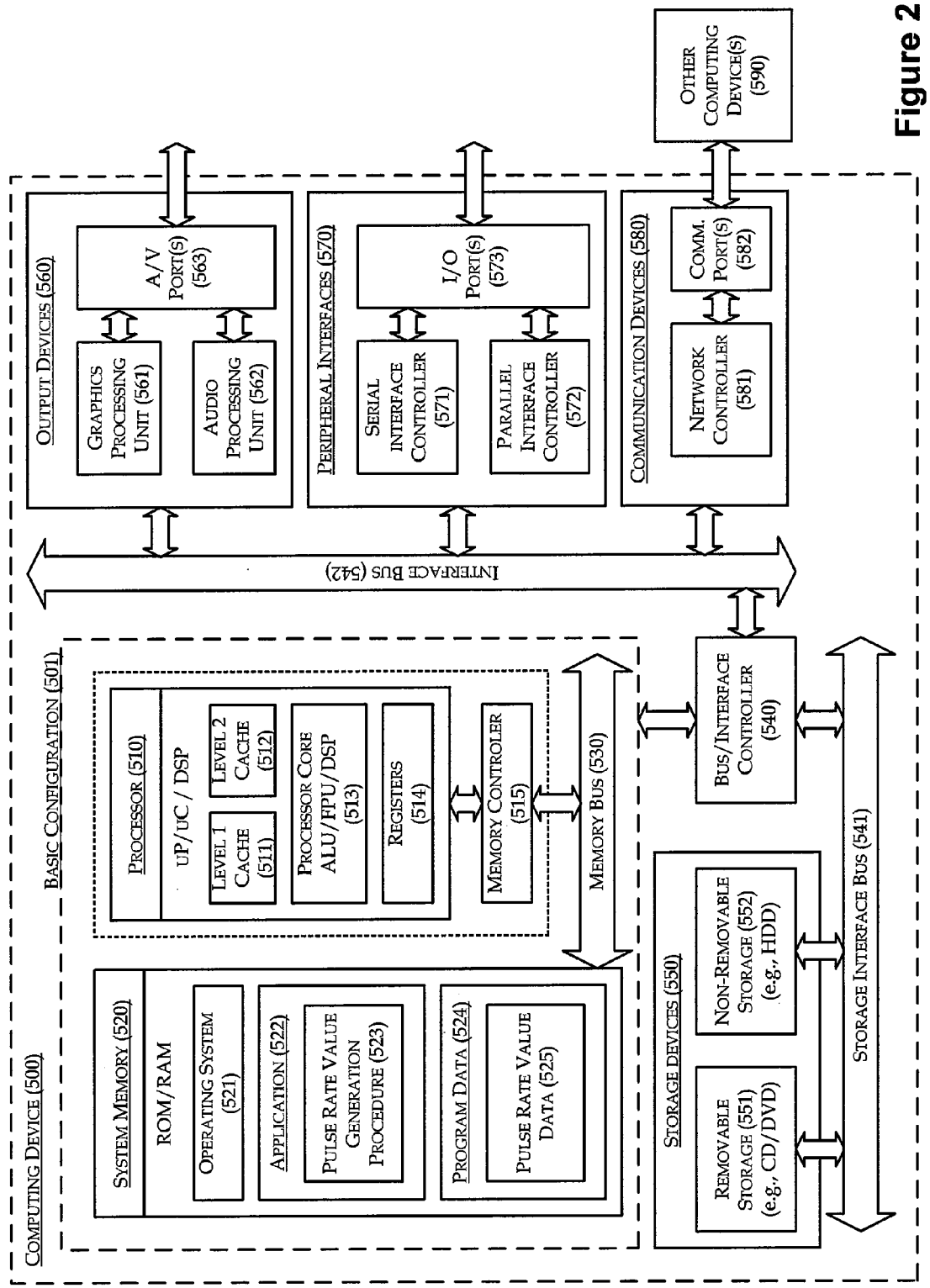
FIG. 2 is a block diagram illustrating an example computing device 500 that is arranged for computing or storing a pulse rate value in accordance with the present disclosure.

FIG. 2 is a block diagram illustrating an example computing device 500 that is arranged for computing or storing a pulse rate value in accordance with the present disclosure. In a configuration 501, computing device 500 may include one or more processors 510 and system memory 520. A memory bus 530 may be used for communicating between the processor 510 and the system memory 520.

Depending on the desired configuration, processor 510 may be of any type including but not limited to a microprocessor (μP), a microcontroller (μC), a digital signal processor (DSP), or any combination thereof. Processor 510 may include one more levels of caching, such as a level one cache 511 and a level two cache 512, a processor core 513, and registers 514. An example processor core 513 may include an arithmetic logic unit (ALU), a floating point unit (FPU), a digital signal processing core (DSP Core), or any combination thereof. An example memory controller 515 may also be used with the processor 510, or in some implementations the memory controller 515 may be an internal part of the processor 510.

Depending on the desired configuration, the system memory 520 may be of any type including but not limited to volatile memory (such as RAM), non-volatile memory (such as ROM, flash memory, etc.) or any combination thereof. System memory 520 may include an operating system 521, one or more applications 522, and program data 524. Application 522 may include a pulse rate value generation procedure that is arranged to determine a pulse rate value based on a detection signal received from a detector. The pulse rate value generation procedure may, for example, access a look-up table to determine a pulse rate value based on a received detection signal. Other procedures may also be used. Program data 524 may include pulse rate value data 525 that may be useful for determining a pulse rate value based on a received detection signal, such as a look-up table or experimental data. In some embodiments, application 522 may be arranged to operate with program data 524 on an operating system 521 such that a pulse rate value is generated based on a detection signal. This described configuration is illustrated in FIG. 2 by those components within dashed line 501.

Computing device 500 may have additional features or functionality, and additional interfaces to facilitate communications between the basic configuration 501 and any required devices and interfaces. For example, a bus/interface controller 540 may be used to facilitate communications between the basic configuration 501 and one or more data storage devices 550 via a storage interface bus 541. The data storage devices 550 may be removable storage devices 551, non-removable storage devices 552, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 520, removable storage 551 and non-removable storage 552 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of device 500.

Computing device 500 may also include an interface bus 542 for facilitating communication from various interface devices (e.g., output interfaces, peripheral interfaces, and communication interfaces) to the basic configuration 501 via the bus/interface controller 540. Example output devices 560 include a graphics processing unit 561 and an audio processing unit 562, which may be configured to communicate to various external devices such as a display or speakers via one or more A/V ports 563. Example peripheral interfaces 570 include a serial interface controller 571 or a parallel interface controller 572, which may be configured to communicate with external devices such as input devices (e.g., keyboard, mouse, pen, voice input device, touch input device, etc.) or other peripheral devices (e.g., printer, scanner, etc.) via one or more I/O ports 573. An example communication device 580 includes a network controller 581, which may be arranged to facilitate communications with one or more other computing devices 590 over a network communication link via one or more communication ports 582.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 500 may also be implemented as a personal computer including both laptop computer and non-laptop computer configurations.

Figure 3:
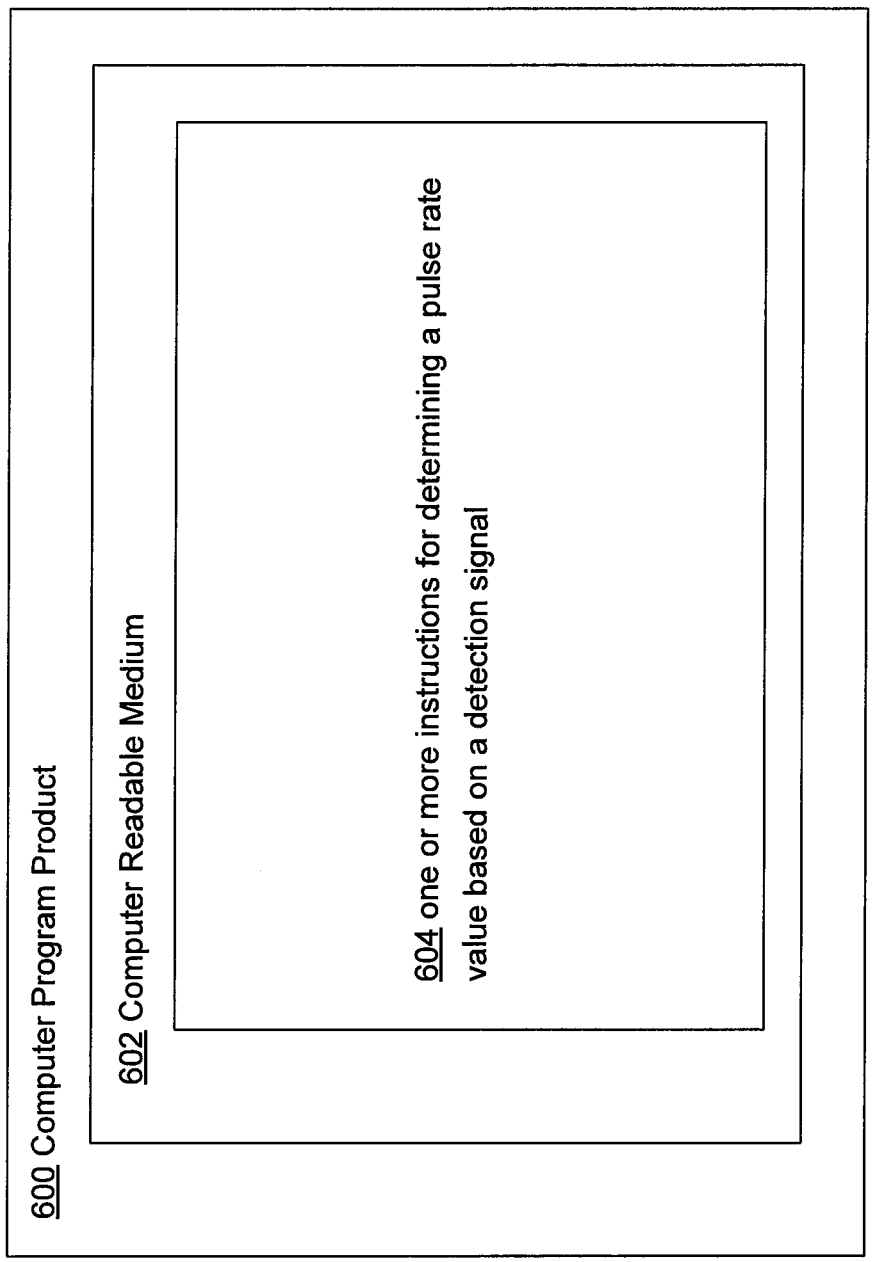
FIG. 3 is a block diagram illustrating an example computer program product 600 that is arranged to store instructions for determining a pulse rate value based on a detection signal in accordance with the present disclosure.

FIG. 3 is a block diagram illustrating an example computer program product 600 that is arranged to store instructions for determining a pulse rate value based on a detection signal in accordance with the present disclosure. The computer readable medium 602 stores instructions 604 that may configure the processing unit to perform all or some of the processes previously described. These instructions may include, for example, one or more executable instructions for determining a pulse rate value based on a detection signal. The instructions may include accessing a look-up table to associate the detection signal with a pulse rate value.

Figure 4:
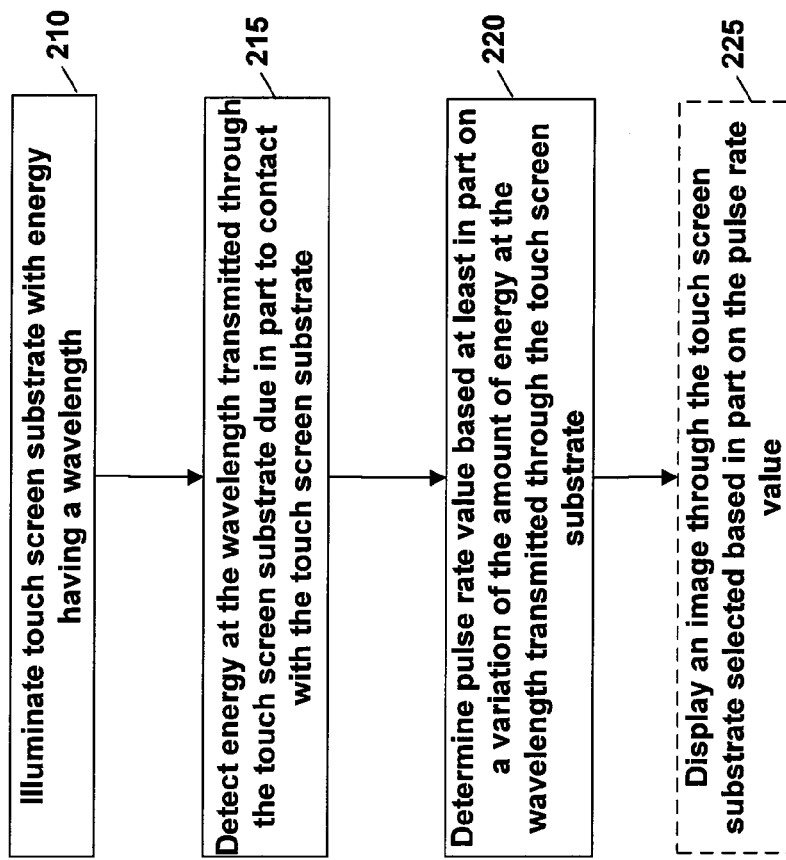
FIG. 4 is a flowchart of an example method of using a touch screen interface to determine a pulse rate value.

FIG. 4 flowchart of an example method of using a touch screen interface to determine a pulse rate value. The example method may be utilized with the touch screen interface 100 described previously for FIG. 1, or other similarly arranged touch screen devices. The example method may include one or more of blocks 210, 215, 220 and 225.

At block 210, the touch screen substrate may be illuminated with optical energy having a wavelength that is appropriate for pulse detection. As described above, this wavelength may be 910 nm, 660 nm, or other wavelength of energy whose amplitude may vary in time with changes in a pulse rate.

At block 215, optical energy transmitted through the touch screen substrate at the requisite wavelength, at least in part due to the user contact with the substrate may be detected 215. At block 220, a pulse rate may be determined based at least in part on variations in the detected energy over time. At block 225, an image may then be displayed through the touch screen substrate that may be selected based in part on the determined pulse rate value. The image may be representative of the pulse rate value, or in some cases an image is displayed (such as a suggestion to a user) that is based on the pulse rate value, but not necessarily representative of the pulse rate value. As described above, the determined pulse rate value may in addition or alternatively be stored in memory, displayed elsewhere, or communicated to another device, or combinations thereof.

Figure 5:
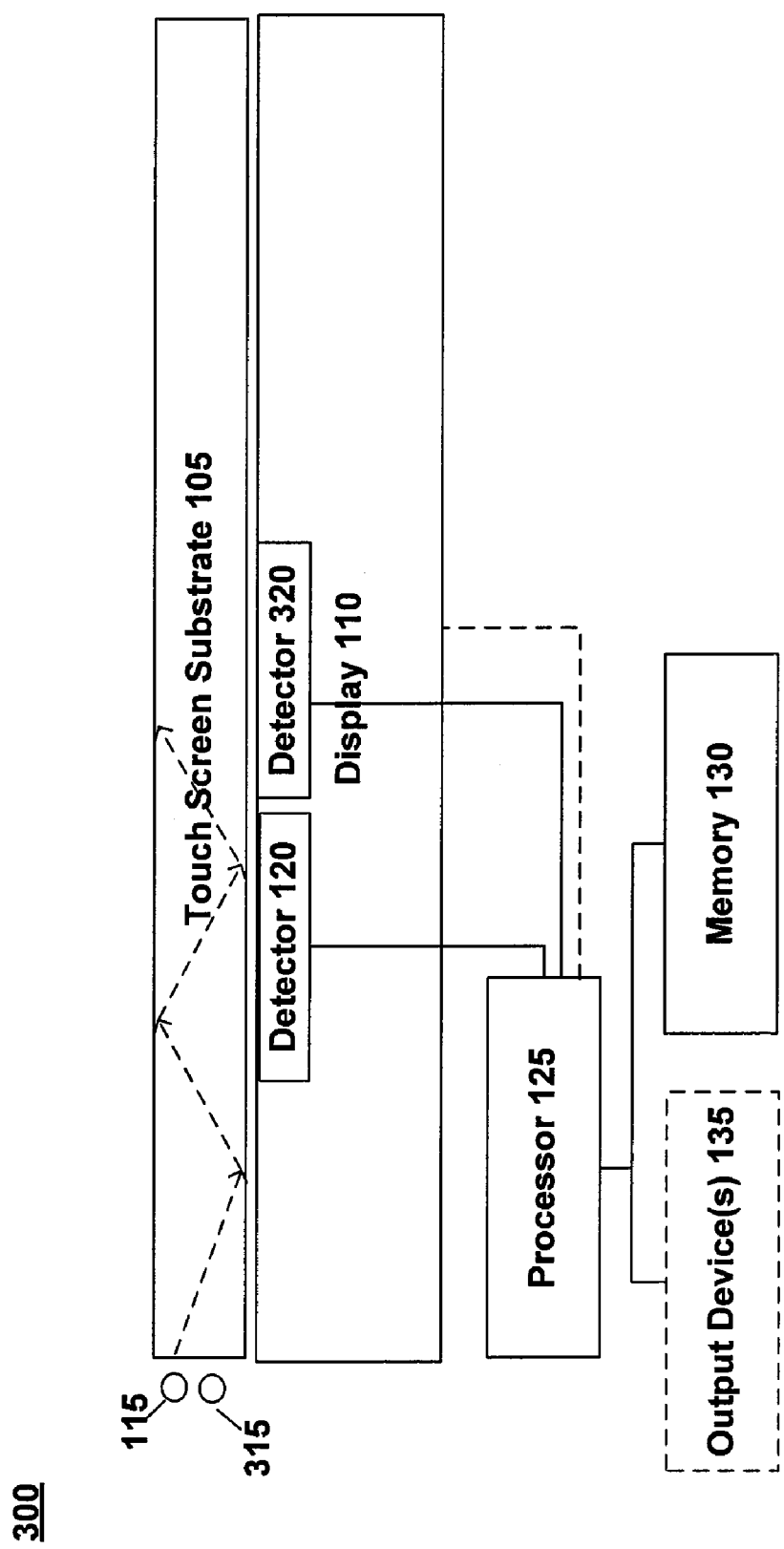
FIG. 5 is a schematic illustration of an example of a touch screen interface that may be used to detect a blood oxygen level of a user.

FIG. 5 is a schematic illustration of an example of a touch screen interface that may be used to detect a blood oxygen level of a user, in accordance with at least some embodiments of the present disclosure. An example of a cross-sectional portion of the touch screen interface 300 is also illustrated. FIG. 5 is intended to be explanatory and is not drawn to scale.

The touch screen interface 300 may have many similar elements to the example of the touch screen interface 100 of FIG. 1, and similar elements will not be described in detail again with reference to FIG. 5. However, the example of FIG. 5 is configured for the detection of a blood oxygen level associated with a user by providing for the illumination of the touch screen substrate 105 with optical energy sources emitting at multiple wavelengths. Detectors may then be used to detect differences in the amount of energy transmitted through the touch screen substrate 105 at the different wavelengths.

Accordingly, in the example of FIG. 5, two optical energy sources 115 and 315 may be positioned effective to illuminate the touch screen substrate 105. An example of suitable optical energy sources may be light emitting diodes (LEDs). The two optical energy sources 115 and 315 may be arranged to emit energy at different wavelengths.

Although FIG. 5 illustrates single optical energy sources for emitting light at each wavelength, any number of additional optical energy sources may be provided for emitting light at additional wavelengths, which may be positioned along a length or width of the touch screen substrate 105. In some examples, a single optical energy source may be arranged to emit light at multiple wavelengths.

The optical energy sources 115 and 315 may be arranged to emit light having a wavelength that is absorbed differently by oxygenated and deoxygenated hemoglobin. Pulse oximeters can make use of 660 nm and 910 nm light. Accordingly, the optical energy source 115 may be configured to emit energy having a wavelength of 660 nm while the light source 315 may be configured to emit energy having a wavelength of 910 nm. The oxygenated blood may reflect more of the 660 nm light than deoxygenated blood, while deoxygenated blood may reflect more of the 910 nm light than oxygenated blood. Other wavelengths may also be used that are appropriate for blood oxygen level detection in other examples.

In some examples, two detectors 120 and 320 may be provided to sense the light transmitted through the touch screen substrate 115 caused in part by the contact by the user. One of the detectors may be relatively insensitive to energy at one of the wavelengths emitted by the optical energy sources 115 and 315. For example, an InGaAs CCD type of detector may be used as one of the detectors, which is sensitive to 910 nm light but relatively insensitive to 660 nm light. Accordingly, the detectors 120 and 320 may provide one or more detection signals that may be used to determine a difference in detected light of each wavelength. Although a single detector 120 and 320 for each wavelength is shown in FIG. 1, an array of detectors may be present adjacent to the touch screen substrate 105 to detect light transmitted through the touch screen substrate responsive to user contact. By providing an array of detectors, a location of the contact may also be determined. In other examples, detectors may be provided around a perimeter of the touch screen substrate 105. Generally, the detectors 120 and 320 may be positioned anywhere that they may receive energy transmitted through the touch screen substrate 105 and any number may be provided. In some additional examples, an array of such detectors may also be arranged to provide location information about the contact by the user. In some further examples, the detectors 120 and 320 may not be arranged to provide location information about the contact by the user, and location information may be obtained by resistive or capacitive sensors (not shown in FIG. 5). Further, although two detectors are used in the example of FIG. 5, in some examples a single detector may be used and later processing may separate out the wavelength components of the received signal. That is, a single detector may be provided that may be sensitive to both illumination wavelengths. The optical energy sources 115 and 315 may be pulsed such that the two energy sources may not illuminate the touch screen substrate simultaneously. In one example, the pulsing occurs on a millisecond timescale. The output of the single detector may then be synchronized to the energy source pulse information, and responses to the two different energy wavelengths identified and analyzed. That is, output of the single detector during illumination with the first wavelength may represent a response to the first wavelength, and output of the single detector during illumination with the second wavelength may represent a response to the second wavelength.

As with the example in FIG. 1, the detectors 120 and 320 may also be positioned in different locations, such as positions effective to receive energy transmitted through a portion of the touch screen substrate 105.

The processor 125 may be coupled to the detectors 120 and 130, and arranged to utilize signals received from the detectors 120 and 320 to determine a blood oxygen level of a user who made contact with the touch screen substrate 105. In particular, one of the detectors 120 and 320 may be relatively insensitive to at least one of the energy wavelengths emitted by the optical energy sources 115 and 315. Any suitable method for determining a blood oxygen level based on different absorption or reflectance of two energy wavelengths may then be implemented by the processor. By analyzing the different characteristics of energy emission at the different wavelengths (e.g., two or more wavelengths), the processor 125 may determine a blood oxygen level of the user who contacted the touch screen substrate 105.

A memory 130 may be coupled to the processor 125. The memory 130 may be storing computer readable instructions, that, when executed, cause the processor 125 to receive signals from the detectors 120 and 320 and determine a blood oxygen level based on one or more differences in the received signals. The memory 130 may be encoded with instructions for computing the blood oxygen level or a look-up table (LUT) for correlating measured signal differences associated with a blood oxygen level, for example. The memory 130 may also be arranged to store a value associated with the blood oxygen level (i.e., a blood oxygen level value) of the user. More than one blood oxygen level value may be stored in memory 130, for example, when a user contacts a touch screen multiple times over the course of a given use. Detected changes in blood oxygen level values may be used by the processor 125 to present a graphical representation of one or more blood oxygen level values on the display 110 or other components of a device in which the touch screen interface 100 may be used. For example, a numerical display or one or more graphical plots may be generated and displayed on the display 110 containing information about one or more blood oxygen level values.

The touch screen interface 300 shown in FIG. 5 may be used to determine a blood oxygen level value associated with a user contacting the touch screen substrate 105. Once a blood oxygen level has been determined, the determined blood oxygen level (i.e., the blood oxygen level value) may be output to one or more output devices 135, which may include another display or a network connection for communication to remote devices. In some examples, the determined blood oxygen level may be displayed on the display 110. Based on the determined blood oxygen level, an image displayed on the display 110 may be altered. Examples of applications, methods or processes for using the touch screen interface 300 will be discussed further below. Additionally, the computing device 500 of FIG. 2 may also be used with the touch screen interface of FIG. 5.

Figure 6:
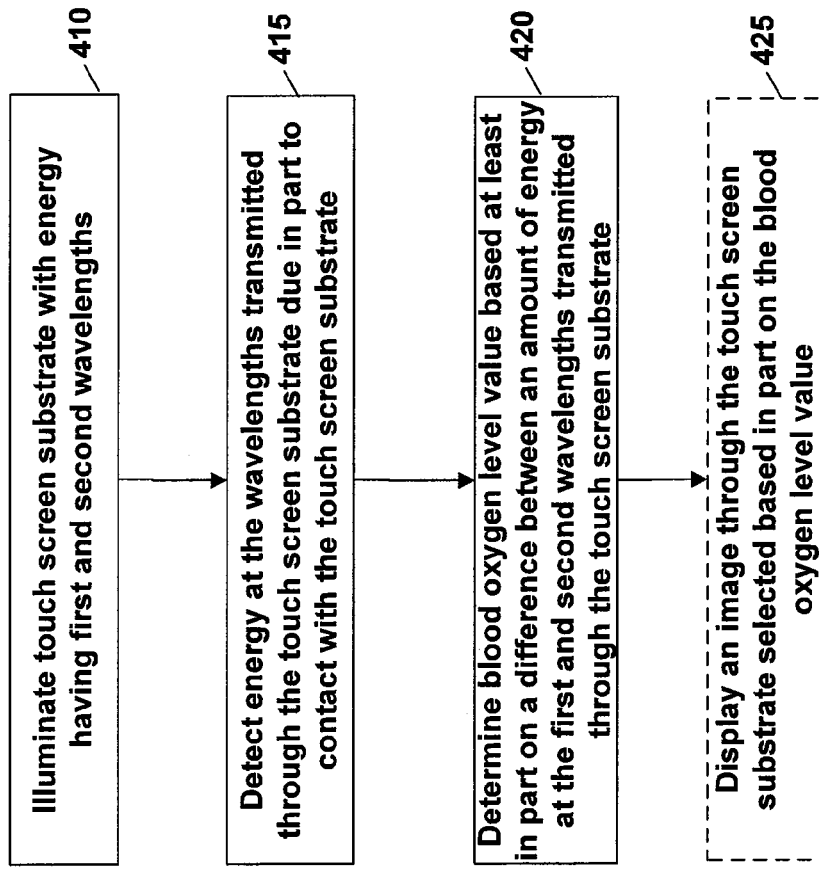
FIG. 6 is a flowchart of an example method of using a touch screen interface to determine a blood oxygen level of a user, all arranged in accordance with at least some embodiments of the present disclosure.

FIG. 6 is a flowchart of an example method of using a touch screen interface to determine blood oxygen level of a user, in accordance with at least some embodiments of the present disclosure. The example method may be utilized with the touch screen interface 300 previously described for FIG. 5, or other similarly arranged touch screen devices. The example method may include one or more of blocks 410, 415, 420, and 425.

At block 410, the touch screen substrate may be illuminated with optical energy having at least a first wavelength and a second wavelength. As described above, these wavelengths may be 910 nm and 660 nm, or other wavelengths of energy that will be absorbed differently by oxygenated and deoxygenated blood.

At block 415, optical energy transmitted through the touch screen substrate at the requisite wavelengths, in part due to contact with the substrate may be detected. At block 420, a blood oxygen level value may be determined based at least in part on differences between the amounts of energy at each of the various wavelengths detected over time. At block 425, an image may then be displayed through the touch screen substrate that may be selected based in part on the determined blood oxygen level value. As described above, the determined blood oxygen level in addition or alternatively may be stored in memory, displayed elsewhere, or communicated to another device, or combinations thereof.

Accordingly, examples of touch screen interfaces have been described above that may be configured to determine a blood oxygen level value or a pulse rate value associated with a user in addition to sensing the location of a touch. In other examples, touch screen interfaces may be provided that may determine both blood oxygen level values and pulse rate values corresponding to the user. In some examples, the same processor may be used to calculate both blood oxygen level value and pulse rate value. In other examples, different processors may be used. The term user is employed herein to refer to any object capable of having a pulse rate, blood oxygen level, or both, that may come into contact with the touch screen substrate.

Examples of touch screen interfaces capable of measuring pulse rate, blood oxygen level, or both, may be employed in a variety of devices including, but not limited to, exercise equipment, appliances, auto or aeronautical control devices, phones, digital assistants, or kiosks.

Touch screen interfaces capable of pulse rate, blood oxygen level, or both measurements may find a variety of uses. For example, the measurements may be used as an indication of a user's health. If deployed on a piece of exercise equipment, a processor included in the machine may emit a control signal causing the machine to select or change a resistance or endurance value, or both, based on the measured pulse rate, blood oxygen level, or both.

As another example, the processor 125 included in the touch screen interfaces 100 and 300 may be able to analyze changes in pulse rate over time. Increasing pulse rate may indicate frustration with the interface 100 or 300. Accordingly, the processor 125 may couple a control signal to the display 110 causing display of an apologetic message, or a recommendation to change the user's action.

From the foregoing it will be appreciated that, although specific embodiments of the invention have been described herein for purposes of illustration, various modifications may be made without deviating from the spirit and scope of the invention. For example, the use of pulse rate and blood oxygen levels have been described above. However, pulse oximetry techniques may be used to analyze other components of a user's blood, such as carbon monoxide. Generally, any number of wavelengths and suitable detectors may be used in conjunction with a touch screen interface to obtain any type of biological information suitable for measurement with pulse oximetry techniques.

Claimed subject matter is not limited in scope to the particular implementations described herein. For example, some implementations may be in hardware, such as employed to operate on a device or combination of devices, for example, whereas other implementations may be in software and/or firmware. Likewise, although claimed subject matter is not limited in scope in this respect, some implementations may include one or more articles, such as a storage medium or storage media. This storage media, such as CD-ROMs, computer disks, flash memory, or the like, for example, may have instructions stored thereon, that, when executed by a system, such as a computer device, a computing system, a computing platform, or other system, for example, may result in execution of a processor in accordance with claimed subject matter, such as one of the implementations previously described, for example. As one possibility, a computing device may include one or more processing units or processors, one or more input/output devices, such as a display, a keyboard and/or a mouse, and one or more memories, such as static random access memory, dynamic random access memory, flash memory, and/or a hard drive.

In the preceding description, various aspects of claimed subject matter have been described. For purposes of explanation, specific numbers, systems and/or configurations were set forth to provide a thorough understanding of claimed subject matter. However, it should be apparent to one skilled in the art and having the benefit of this disclosure that claimed subject matter may be practiced without the specific details. In other instances, well-known features were omitted and/or simplified so as not to obscure claimed subject matter. While certain features have been illustrated and/or described herein, many modifications, substitutions, changes and/or equivalents will now, or in the future, occur to those skilled in the art. It is, therefore, to be understood that the appended claims are intended to cover all such modifications and/or changes as fall within the true spirit of claimed subject matter.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality may be seen as "associated" with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In some instances, one or more components may be referred to herein as "configured to," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other pasttense adjectives are generally not intended to exclude such variants, unless context dictates otherwise.

What is claimed is:

1. A touch screen interface configured to respond to contact from a user, the touch screen interface comprising:
   a touch screen substrate;
   an optical energy source positioned to illuminate the touch screen substrate to cause optical energy having a specified wavelength to be internally reflected within the touch screen substrate;
   a detector positioned to receive optical energy having the specified wavelength transmitted through the touch screen interface, wherein the detector is arranged to generate a detection signal that is at least in part responsive to contact to the touch screen substrate, wherein the detection signal is indicative of the received optical energy at the specified wavelength; and
   a processor coupled to the detector and configured to receive the detection signal from the detector, and determine a pulse rate associated with the user based at least in part on the detection signal received from the detector.

2. The touch screen interface of claim 1 wherein the processor is further configured to determine a location of the contact based at least in part on the first detection signal received from the detector.

3. The touch screen interface of claim 1 wherein the touch screen substrate is positioned adjacent a display.

4. The touch screen interface of claim 3 wherein the detector is integrated in the display.

5. The touch screen interface of claim 1 wherein the specified wavelength is either 660 nm or 910 nm.

6. The touch screen interface of claim 1 wherein the processor is configured to determine the pulse rate associated with the user based at least in part on a determined change in amplitude of the detection signal over time.

7. The touch screen interface of claim 1 wherein the detector comprises a charge-coupled device (CCD).

8. The touch screen interface of claim 1 wherein the optical energy source comprises a light-emitting diode (LED).

9. The touch screen interface of claim 1, wherein the optical energy source is further arranged to illuminate the touch screen with optical energy having another specified wavelength, wherein the detector is further arranged to receive optical energy from the touch screen interface having the other specified wavelength, wherein the detector is further arranged to generate another detection signal that is at least in part responsive to contact to the touch screen substrate, wherein the other detection signal is indicative of the received optical energy at the other specified wavelength, and wherein the processor is further configured to receive the other detection signal from the detector and determine a blood oxygen level based in part on the first detection signal and the second detection signals received from the first detector.

10. The touch screen interface of claim 9 wherein the detector is sensitive to energy at both the specified wavelength and the other specified wavelength, and the optical energy source is configured to alternately illuminate the touch screen substrate with optical energy having the specified wavelength and the other specified wavelength.

11. The touch screen interface of claim 9, the detector comprising a first detector and a second detector, wherein the first detector is positioned to receive optical energy transmitted through the touch screen interface corresponding to the specified wavelength, and wherein the second detector is positioned to receive optical energy transmitted through the touch screen interface corresponding to the other specified wavelength.

12. The touch screen interface of claim 9, the optical energy source comprising a first optical energy source and a second optical energy source, wherein the first optical energy source is positioned to illuminate the touch screen substrate with optical energy having the specified wavelength, and wherein the second optical energy source is positioned to illuminate the touch screen substrate with optical energy having the other specified wavelength.

13. The touch screen interface of claim 9, the detector comprising a first detector and a second detector, and the optical energy source comprising a first optical energy source and a second optical energy source, wherein the first detector is positioned to receive optical energy transmitted through the touch screen interface corresponding to the specified wavelength, the second detector is positioned to receive optical energy transmitted through the touch screen interface corresponding to the other specified wavelength, the first optical energy source is positioned to illuminate the touch screen substrate with optical energy having the specified wavelength, and the second optical energy source is positioned to illuminate the touch screen substrate with optical energy having the other specified wavelength.

14. The touch screen interface of claim 9 wherein the first wavelength is 910 nm and the second wavelength is 660 nm.

15. A touch screen interface configured to respond to contact from a user, the touch screen interface comprising:
   a touch screen substrate;
   a first optical energy source positioned to illuminate the touch screen substrate with optical energy having a first wavelength;
   a second optical energy source positioned to illuminate the touch screen substrate with optical energy having a second wavelength, wherein at least one of the first optical energy source or the second optical energy source is positioned relative to the touch screen substrate to cause optical energy to be internally reflected within the touch screen substrate;
   a first detector positioned to receive optical energy having the first wavelength transmitted through the touch screen interface, wherein the first detector is arranged to generate a first detection signal that is at least in part responsive to the contact to the touch screen substrate, and the first detection signal is indicative of the received optical energy at the first wavelength; and
   a second detector positioned to receive optical energy having the second wavelength transmitted through the touch screen interface, wherein the detector is arranged to generate a second detection signal that is at least in part responsive to the contact to the touch screen substrate, and the second detection signal is indicative of the received optical energy at the second wavelength.

16. The touch screen interface of claim 15 wherein the first wavelength is 910 nm and the second wavelength is 660 nm.

17. A method for a touch screen interface to detect a pulse rate associated with a user when the user touches the touch screen interface, the method comprising:
   illuminating a touch screen substrate from a first side of the touch screen substrate with optical energy having a specified wavelength for pulse rate detection;
   receiving from a second side different than the first side optical energy transmitted through the touch screen substrate responsive to the contact with the touch screen substrate and generating a detection signal responsive to the received optical energy;
   identifying variations in the detection signal; and
   determining the pulse rate associated with the user based at least in part on the identified variations in the detection signal.

18. The method according to claim 17 further comprising:
   modifying an image displayed through the touch screen substrate, the modification in part based on the determined pulse rate.

19. The method according to claim 17 further comprising:
   storing each determined pulse rate in memory.

20. The method according to claim 19 wherein the specified wavelength is either 910 nm or 660 nm.

21. A method for a touch screen interface to detect either a blood oxygen level associated with a user and/or a pulse rate associated with the user, responsive to a touch to the touch screen interface, the method comprising:
   illuminating a touch screen substrate with optical energy having a first wavelength and a second wavelength such that at least a portion of the optical energy is internally reflected within the touch screen substrate, wherein the first wavelength and the second wavelength are selected appropriately for an indication of blood oxygen level associated with the user;
   detecting optical energy transmitted from the touch screen substrate to generate a detection signal, wherein the detection signal indicates an amount of transmitted optical energy at the first or second wavelengths, wherein the amount of transmitted optical energy at the first or the second wavelengths varies at least in part in response to the touch; and
   determining the blood oxygen level associated with the user from the detection signal based at least part on a difference between the amount of optical energy detected at the first and second wavelengths.

22. The method according to claim 21 wherein the act of illuminating the touch screen substrate with optical energy having the first wavelength and the second wavelength comprises alternately illuminating the touch screen substrate with pulses of optical energy having the first wavelength and pulses of optical energy having the second wavelength.

23. The method according to claim 21 further comprising:
   modifying an image displayed through the touch screen substrate, the modification in part based on the determined blood oxygen level associated with the user.

24. The method according to claim 21 wherein the first and second wavelengths are 910 nm and 660 nm, respectively.

25. The method according to claim 21 further comprising:
   determining the pulse rate associated with the user based at least in part on a variation of the amount of transmitted optical energy at either the first or second wavelength.

26. The touch screen interface of claim 1, wherein the optical energy source is positioned along a first side of the touch screen substrate, and wherein the detector is positioned along a second side of the touch screen substrate different than the first side.

27. The touch screen interface of claim 15, wherein the optical energy source is positioned along a first side of the touch screen substrate, and wherein the detector is positioned along a second side of the touch screen substrate different than the first side.

28. The method of claim 21, wherein said illuminating the touch screen substrate comprises emitting light from a first side of the touch screen substrate, and wherein said detecting optical energy comprises detecting light from a second side of the touch screen substrate different than the first side.

* * * * *

UNITED STATES PATENT AND TRADEMARK OFFICE
CERTIFICATE OF CORRECTION

PATENT NO. : 8,320,985 B2
APPLICATION NO. : 12/417478
DATED : November 27, 2012
INVENTOR(S) : Miller It is certified that error appears in the above-identified patent and that said Letters Patent is hereby corrected as shown below:

In Fig. 2, Sheet 2 of 6, Below "Processor (510)", delete "UP/UC /" and insert -- µP/µC / --, therefor.

In Fig. 2, Sheet 2 of 6, in Box "(515)", in Line 1, delete "CONTROLER" and insert -- CONTROLLER --, therefor.

In Column 2, Line 45, delete "pane." and insert -- panel. --, therefor.

Signed and Sealed this
Second Day of April, 2013

Teresa Stanek Rea
*Acting Director of the United States Patent and Trademark Office*